(12) United States Patent
Hsu et al.

(10) Patent No.: US 9,353,053 B2
(45) Date of Patent: May 31, 2016

(54) THIOLATION METHOD FOR MODIFYING CARBON NANOTUBES

(71) Applicant: NATIONAL TSING HUA UNIVERSITY, Hsinchu (TW)

(72) Inventors: Ming-Hua Hsu, Hsinchu (TW); Hong Chuang, Kinmen County (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 14/533,069

(22) Filed: Nov. 4, 2014

(65) Prior Publication Data
US 2016/0075646 A1    Mar. 17, 2016

(30) Foreign Application Priority Data
Sep. 12, 2014  (TW) .............................. 103131593 A (51) Int. Cl.
*C07C 319/08*    (2006.01)
(52) U.S. Cl.
CPC ..................................... *C07C 319/08* (2013.01)
(58) Field of Classification Search
None
See application file for complete search history.

(56) References Cited

U.S. PATENT DOCUMENTS

| 4,868,310 A * | 9/1989 | Chang | C07D 275/03 548/213 |
|---|---|---|---|
| 2009/0280593 A1* | 11/2009 | Serban | G01N 29/022 438/49 |

FOREIGN PATENT DOCUMENTS

KR    1020010102598 A  *  11/2001

OTHER PUBLICATIONS

Lim et al. ("Selective thiolation of single-walled carbon nanotubes", Synthetic Metals, vol. 139, 2003, pp. 521-527); Chang (U.S. Pat. No. 4,868,310).*
Robinsonbrothers (Endeavour Specialty Chemicals, Sulfur Chemistry 2012, 12 pages).*
Curran et al. ("Thiolation of carbon nanotubes and sidewall functionalization", J. Material Res., vol. 21, No. 4, Apr. 2006, pp. 1012-1018).*
Kim et al. ("Surface thiolation of carbon nanotubes as supports: A promising route for the high dispersion of Pt nanoparticles for electrocatalysts", Journal of Catalysis, vol. 238, Jan. 2006, pp. 394-401).*
Ming-Hua Hsu et al., "Simple and Highly Efficient Direct Thiolation of the Surface of Carbon Nanotubes", RSC Advances, Mar. 13, 2014, pp. 14777-14780.

* cited by examiner

*Primary Examiner* — Rosalynd Keys
(74) *Attorney, Agent, or Firm* — CKC & Partners Co., Ltd.

(57) ABSTRACT

A thiolation method for modifying carbon nanotubes includes steps as follows. A carboxylation step is provided, wherein the carbon nanotubes are reacted with an oxidant for generating carboxyl groups on surfaces of the carbon nanotubes so as to form carboxylated carbon nanotubes. A hydroxylation step is provided, wherein the carboxyl groups are transformed into hydroxyl groups so as to transform the carboxylated carbon nanotubes into hydroxylated carbon nanotubes. A thiolation step is provided, wherein the hydroxylated carbon nanotubes, a sulfur source and a first acidic substance are mixed and then stirred so as to form a first mixture, the first mixture is added portion-wisely into an alkaline solution so as to form a second mixture, and the second mixture is acidified so as to form an acidified solution having a pH value ranging from 2 to 3, thus the hydroxylated carbon nanotubes are transformed into thiolated carbon nanotubes.

21 Claims, 9 Drawing Sheets

THIOLATION METHOD FOR MODIFYING CARBON NANOTUBES

RELATED APPLICATIONS

This application claims priority to Taiwan Application Serial Number 103131593, filed Sep. 12, 2014, which is herein incorporated by reference.

BACKGROUND

1. Technical Field

The present disclosure relates to a method for modifying carbon nanotubes. More particularly, the present disclosure relates to a thiolation method for modifying carbon nanotubes.

2. Description of Related Art

Carbon nanotubes (CNTs) have been widely applied in numerous scientific and technological fields since being discovered. The CNTs exhibit excellent physical, thermal, and electrical properties, and thus can be applied to manufacture one-dimensional nanomaterials, novel electronic elements and devices, such as carbon nanotube field effect transistor (CNTFET) and carbon nanotube computer. The CNTs can also be applied to manufacture support materials for fuel cells or heterogeneous catalysts.

Thiol groups (—SH) exhibit excellent affinity with gold, and have been applied to self-assembly and conjugation. If the CNTs can be modified with the thiol groups, the application thereof can be broadened.

The surfaces of the CNTs can be modified with thiol groups by methods as follows. In a first method, phospholipid molecules are conjugated on the surfaces of the CNTs by noncovalent adsorption. The CNTs can be conjugated with DNA via the phospholipid molecules. However, the bonding strength of the noncovalent adsorption is weak, and thus a second method based on covalent bond is developed. In the second method, the surfaces of the CNTs are typically oxidized by an acidic mixture (sulfuric acid and nitric acid) so as to generate carboxyl groups on the surfaces of the CNTs. The carboxyl groups can be conjugated with a thiol group-containing linker through an amide bond. However, in the first and the second methods, the thiol groups are conjugated on the surfaces of the CNTs via space linkers. In other words, the thiol groups cannot be directly conjugated on the surfaces of the CNTs. When the thiolated CNTs are applied to conjugate with gold nanoparticles, a resistance between the thiolated CNTs and the gold nanoparticles may be excessive.

A third method for directly modifying the surfaces of the CNTs is developed, in which a mixture of single-wall CNTs and sulfur is treated with plasma. However, a specific equipment is required for the third method, and the specific equipment is expensive. Accordingly, it is unfavorable to apply the third method to mass production and the production cost thereof remains high.

Therefore, how to directly modify the surfaces of the CNTs with thiol groups, which is favorable to apply to mass production and has low production cost, has become an important goal of relevant academia and industry.

SUMMARY

According to one aspect of the present disclosure, a thiolation method for modifying carbon nanotubes includes steps as follows. A carboxylation step is provided, wherein the carbon nanotubes are reacted with an oxidant for generating carboxyl groups on surfaces of the carbon nanotubes so as to form carboxylated carbon nanotubes. A hydroxylation step is provided, wherein the carboxyl groups of the carboxylated carbon nanotubes are transformed into hydroxyl groups so as to transform the carboxylated carbon nanotubes into hydroxylated carbon nanotubes. A thiolation step is provided. The thiolation step includes steps as follows. The hydroxylated carbon nanotubes, a sulfur source and a first acidic substance are mixed and then stirred at a temperature ranging from 125° C. to 160° C. for 36 hours to 60 hours so as to form a first mixture. The first mixture is added portion-wisely into an alkaline solution at a temperature ranging from 0 to 35° C. for 12 hours to 36 hours so as to form a second mixture. The second mixture is acidified so as to form an acidified solution having a pH value ranging from 2 to 3. Thus the hydroxylated carbon nanotubes are transformed into thiolated carbon nanotubes.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1:
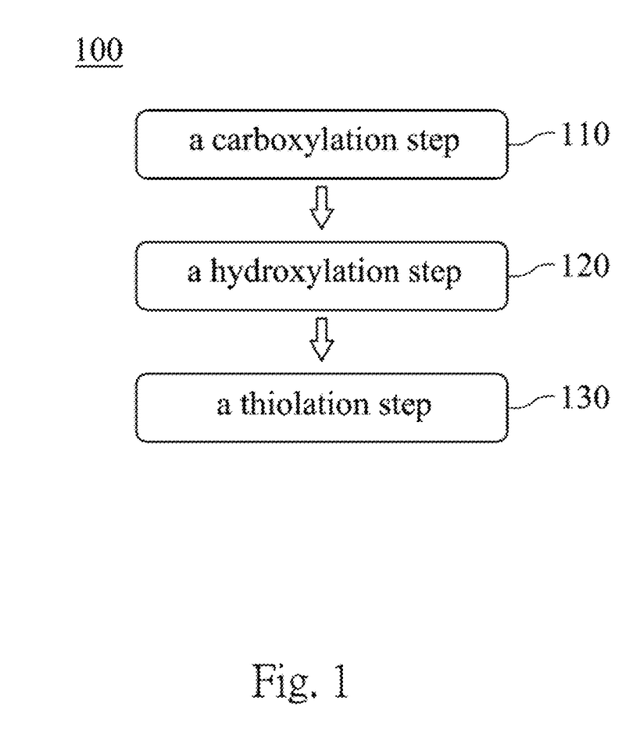
FIG. 1 is a flow diagram showing a thiolation method for modifying carbon nanotubes according to one embodiment of the present disclosure.

FIG. 1 is a flow diagram showing a thiolation method 100 for modifying carbon nanotubes according to one embodiment of the present disclosure. In FIG. 1, the thiolation method 100 for modifying the carbon nanotubes includes carboxylation step 110, a hydroxylation step 120 and a thiolation step 130.

First, the carboxylation step 110 is provided, wherein the carbon nanotubes are reacted with an oxidant for generating carboxyl groups on surfaces of the carbon nanotubes so as to form carboxylated carbon nanotubes. An average outer diameter of the carbon nanotubes is greater than 0 nm and less than 8 nm, and an average length of the carbon nanotubes ranges from 10 μm to 30 μm. Therefore, it is favorable to applied to nanotechnologies. The oxidant can be an acid, ozone, potassium permanganate (kMnO$_4$), potassium dichromate (K$_2$Cr$_2$O$_7$) or a mixture of sulfuric acid (H$_2$SO$_4$) and hydrogen peroxide (H$_2$O$_2$). In the mixture of the H$_2$SO$_4$ and, the H$_2$O$_2$, a volume ratio of the H$_2$SO$_4$ to the H$_2$O$_2$ ranges from 3:1 to 4:1. When the oxidant is the acid, the acid can be H$_2$SO$_4$, nitric acid (HNO$_3$), perchloric acid (HClO$_4$), hydrochloric acid (HCl) or a mixture thereof. Furthermore, the carboxylation step 110 can be conducted at a temperature ranging from 15° C. to 120° C. for 3 hours to 84 hours. The time and the temperature for conducting the carboxylation step 110 can be adjusted according to the oxidant.

Second, the hydroxylation step 120 is provided, herein the carboxyl groups of the carboxylated carbon nanotubes are transformed into hydroxyl groups so as to transform the carboxylated carbon nanotubes into hydroxylated carbon nanotubes.

Figure 2:
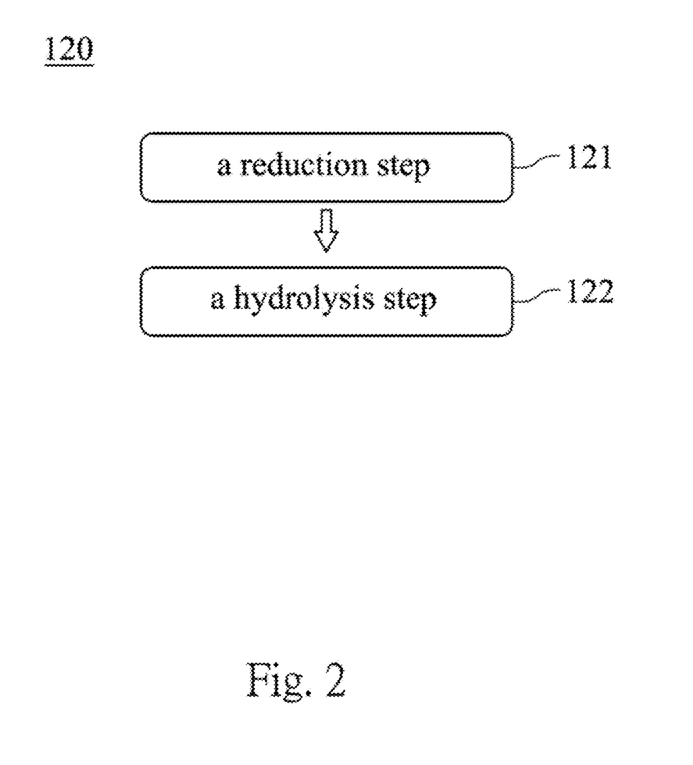
FIG. 2 is a flow diagram showing a hydroxylation step of the thiolation method for modifying the carbon nanotubes in FIG. 1.

FIG. 2 is a flow diagram showing the hydroxylation step 120 of the thiolation method 100 for modifying the carbon nanotubes in FIG. 1. In FIG. 2, the hydroxylation step 120 includes a reduction step 121 and a hydrolysis step 122.

The reduction step 121 is provided, wherein the carboxylated carbon nanotubes, a reductant and a first solvent are mixed, and the carboxyl groups of the carboxylated carbon nanotubes are reduced so as to form a reaction solution. The reductant can be lithium aluminium hydride (LiAlH$_4$), borane (BH$_3$), sodium tetrahydridoborate (NaBH$_4$) or a Fenton reagent. The Fenton reagent can be an acidic mixture of ferrous sulfate and hydrogen peroxide. According to one example of the present disclosure, the ratio of the ferrous sulfate to the hydrogen peroxide (30 vol %) of the Fenton reagent is 1 gram to 1 milliliter, and a pH value of the Fenton reagent is adjusted to less than 3 with concentrated sulfuric acid. The first solvent can be anhydrous ether or anhydrous tetrahydrofuran, Furthermore, the reduction step 121 can be conducted at a temperature ranging from 40° C. to 80° C. for 20 hours to 30 hours.

The hydrolysis step 122 is provided, wherein a second acidic substance is added into the reaction solution so as to obtain the hydroxylated carbon nanotubes. The second acidic substance can be hydrochloric acid, sulfuric acid, hydrobromic acid (HBr), hydroiodic acid (HI) or acetic acid (CH$_3$COOH).

Referring back to FIG. 1, the thiolation step 130 is provided. The thiolation step 130 includes steps as follows. First, the hydroxylated carbon nanotubes, a sulfur source and a first acidic substance are mixed and then stirred at a temperature ranging from 125° C. to 160° C. for 36 hours to 60 hours so as to form a first mixture. The sulfur source can be thiourea (CH$_4$N$_2$S) or thioacetic acid (C$_2$H$_4$OS). The first acidic substance can be hydrobromic acid, acetic acid, hydroiodic acid, chloric acid (HClO$_3$), perchloric acid, phosphoric acid (H$_3$PO$_4$) or a mixture thereof. A pH value of the first acidic substance can range from 0 to 2. Second, the first mixture is added portion-wisely into an alkaline solution at a temperature ranging from 0° C. to 35° C. for 12 hours to 36 hours so as to form a second mixture. A pH value of the alkaline solution can range from 10 to 14. The alkaline solution can be a sodium hydroxide (NaOH) solution or a potassium hydroxide (KOH) solution. A temperature of the alkaline solution can range from 0° C. to 30° C. A concentration of the alkaline solution can range from 5 weight percentage (wt %) to 30 wt %. Third, the second mixture is acidified so as to form an acidified solution having a pH value ranging from 2 to 3. By the thiolation step 130, the hydroxylated carbon nanotubes are transformed into thiolated carbon nanotubes. The second mixture can be acidified by adding sulfuric acid, hydrochloric acid, hydrobromic acid, hydroiodic acid or acetic acid into the second mixture. A concentration of the sulfuric acid, the hydrochloric acid, the hydrobromic acid, the hydroiodic acid or the acetic acid can range from 35 wt % to 75 wt %. The second mixture can be acidified at a temperature ranging from 0° C. to 15° C.

Figure 3:
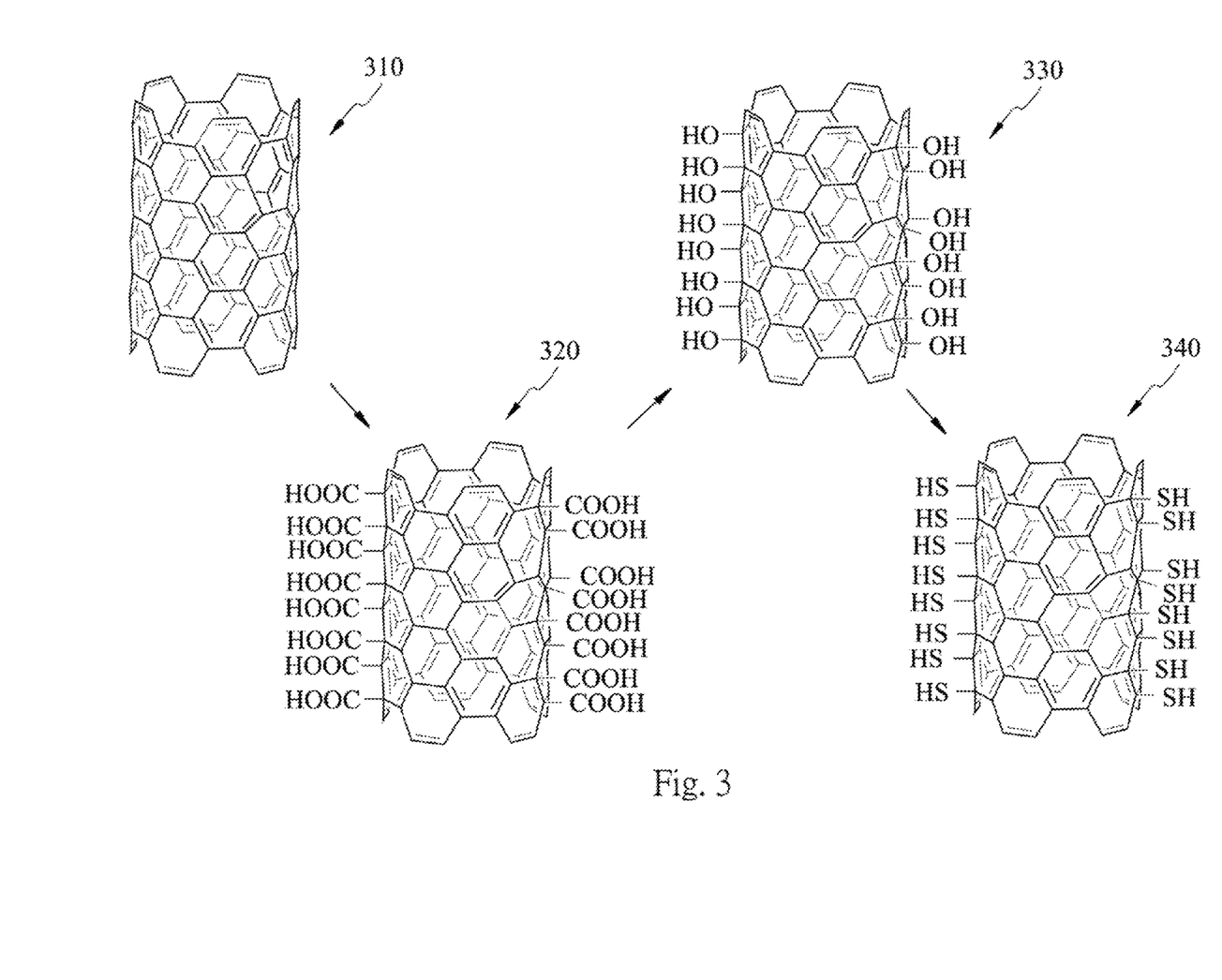
FIG. 3 is a schematic view showing a reaction of a thiolation method for modifying carbon nanotubes according to another embodiment of the present disclosure.

FIG. 3 is a schematic view showing a reaction of a thiolation method for modifying carbon nanotubes according to another embodiment of the present disclosure. For simplifying, only one carbon nanotube 310 is illustrated in FIG. 3. In FIG. 3, the carbon nanotube 310 is transformed into a carboxylated carbon nanotube 320 by a carboxylation step. In the example, at least one carboxyl group and other oxygen-containing groups (such as carbonyl group which is not shown in FIG. 3) are generated on a surface of the carboxylated carbon nanotube 320. After a hydroxylation step, the carboxyl group and the other oxygen-containing groups are transformed into hydroxyl groups, so that the carboxylated carbon nanotube 320 is transformed into a hydroxylated carbon nanotube 330. After a thiolation step, the hydroxyl groups are transformed into thiol groups, so that the hydroxylated carbon nanotube 330 is transformed into a thiolated carbon nanotube 340. In FIG. 3, a number of the functional groups (the carboxyl groups, the hydroxyl groups and the thiol groups) on the surface of the carboxylated carbon nanotube 320, the hydroxylated carbon nanotube 330 and the thiolated carbon nanotube 340 is only for example, and the number of the functional groups is not limited as that shown in FIG. 3.

Figure 4:
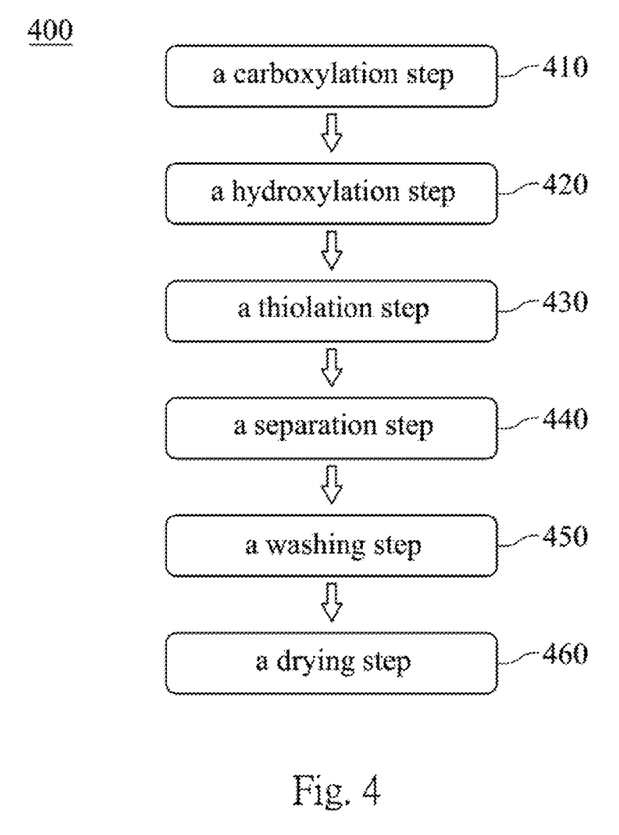
FIG. 4 is a flow diagram showing a thiolation method for modifying carbon nanotubes according to yet another embodiment of the present disclosure.

FIG. 4 is a flow diagram showing a thiolation method 400 for modifying carbon nanotubes according to yet another embodiment of the present disclosure. In FIG. 4, the thiolation method 400 for modifying the carbon nanotubes includes a carboxylation step 410, a hydroxylation step 420, a thiolation step 430, a separation step 440, a washing step 450 and a drying step 460.

The carboxylation step 410, the hydroxylation step 420 and the thiolation step 430 are sequentially provided. The details of the carboxylation step 410, the hydroxylation step 420 and the thiolation step 430 are the same as that of the carboxylation step 110, the hydroxylation step 120, and the thiolation step 130 in FIG. 1, and will not be repeated herein.

The separation step 440 is provided, wherein thiolated carbon nanotubes are separated from an acidified solution. The washing step 450 is provided, wherein the thiolated carbon nanotubes are washed with water. The water can be distilled water or deionized water. The drying step 460 is provided, wherein the thiolated carbon nanotubes washed with the water are heated to dryness The drying step 460 can be conducted at a temperature ranging from 40° C. to 80° C. for 16 hours to 32 hours. In the end, the thiolated carbon nanotubes in a powder state are obtained.

EXAMPLES

Preparation of Thiolated Carbon Nanotubes

First, a plurality of carbon nanotubes are provided. The carbon nanotubes are purchased from Chengdu Organic Chemical Co., Ltd. An average outer diameter of the carbon nanotubes is greater than 0 nm and less than 8 nm, and an average length of the carbon nanotubes ranges from 10 μm to 30 μm.

A carboxylation step is provided. Specifically, the carbon nanotubes (100 mg) and HNO$_3$ (14M, 20.0 mL) are mixed so as to form a suspension solution. The suspension solution is stirred at a temperature ranging from 85° C. to 110° C. for 4 hours to 8 hours. Then the suspension solution is poured into distilled water (500 mL). Pellets are collected by centrifugation at 8,000 rpm and are washed with distilled water for 3 to 5 times. Then the pellets are dried in a vacuum oven at a temperature ranging from 40° C. to 80° C. for 16 hours to 32 hours, so that a first stage product is obtained. The first stage product is mixed with a mixture of $H_2SO_4$ and $H_2O_2$ (30 vol %) so as to form another suspension solution. The volume ratio of the $H_2SO_4$ to the $H_2O_2$ is 4:1 ($H_2SO_4$: 100 mL, $H_2O_2$: 25 mL). The suspension solution formed from the first stage product and the mixture of the $H_2SO_4$ and the $H_2O_2$ is stirred at a temperature ranging from 15° C. to 30° C. for 3 hours to 6 hours, and then is poured into distilled water (500 mL). Pellets are collected by centrifugation at 8,000 rpm and are washed with distilled water for 3 to 5 times. Then the pellets are dried in a vacuum oven at a temperature ranging from 40° C. to 80° C. for 16 hours to 32 hours. By the carboxylation step, carboxylated carbon nanotubes are obtained.

A hydroxylation step is provided. Specifically, the carboxylated carbon nanotubes (80.0 mg), $LiAlH_4$ (303.0 mg, 8.0 mmole) and anhydrous ether (20 mL) are mixed and stirred under reflux at a temperature ranging from 40° C. to 55° C. for 20 hours to 30 hours so as to form a reaction solution. After cooling to room temperature, the reaction solution is hydrolyzed by adding 1.0 N HCl into the reaction solution until no further evolution of hydrogen gas is observed. Pellets are collected by centrifugation at 8,000 rpm and are washed with deionized water several times. Then the pellets are dried in a vacuum oven at a temperature ranging from 40° C. to 80° C. for 16 hours to 32 hours. By the hydroxylation step, hydroxylated carbon nanotubes are obtained.

A thiolation step is provided. Specifically, the hydroxylated carbon nanotubes (300 mg), thiourea (11.4 g, 150 mmol) and a first acidic substance are mixed and stirred under reflux at a temperature ranging from 125 DC to 160° C. for 48 hours so as to form a first mixture. In the example, the first acidic substance is a mixture of HBr (25 mL) and glacial acetic acid (50 mL). The first mixture is added portion-wisely into a 0° C. and 15 wt % aqueous NaOH solution (600 mL) and stirred for 12 hours to 36 hours at room temperature (about 25° C.) so as to form a second mixture. The second mixture is acidified by adding 50 wt % aqueous $H_2SO_4$ so as to form an acidified solution having a pH value ranging from 2 to 3. During acidifying, a temperature of the second mixture is maintained at 0° C. to 10° C. Afterwards, pellets are collected by centrifugation at 8,000 rpm and are washed with distilled water several times. Then the pellets are dried in a vacuum oven at 50° C. for 24 hours. By the thiolation step, thiolated carbon nanotubes are obtained.

Figure 5:
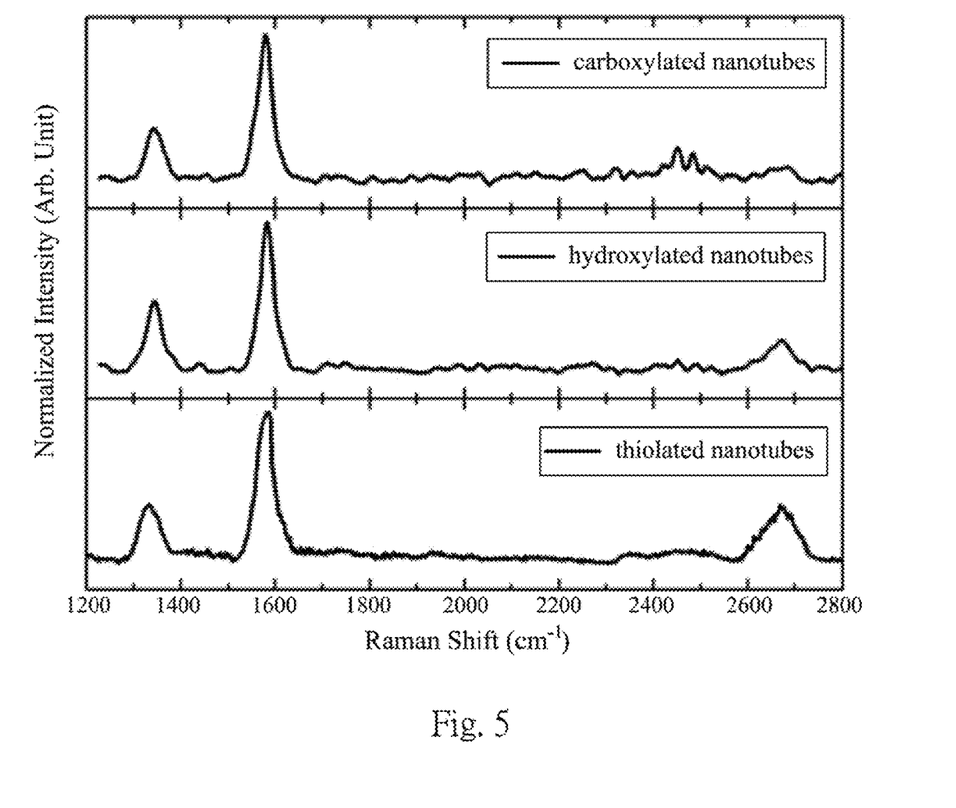
FIG. 5 shows Raman spectra of carboxylated carbon nanotubes, hydroxylated carbon nanotubes and thiolated carbon nanotubes according to one example of the present disclosure.

FIG. 5 shows Raman spectra of the carboxylated carbon nanotubes, the hydroxylated carbon nanotubes and the thiolated carbon nanotubes according to one example of the present disclosure. The carboxylated carbon nanotubes, the hydroxylated carbon nanotubes and the thiolated carbon nanotubes prepared from the above steps are measured with a Raman spectrometer (the excitation source is a 532-nm diode laser, the scattering light is filtered using a long-pass Semrock filter, and the signals are analyzed using a Monochromator DK480). As shown in FIG. 5, the characteristic thiol group signal at 2670 $cm^{-1}$ can be observed from the Raman spectrum of the thiolated carbon nanotubes, which proofs that the thiolation method for modifying the carbon nanotubes according to the present disclosure can successfully modify the surfaces of the carbon nanotubes with thiol groups.

Mixture of Gold Nanoparticles and Thiolated Carbon Nanotubes

First, gold nanoparticles having an average particle size of 13 nm are provided. The gold nanoparticles are obtained by a citrate reduction of $HAuCl_4$. Specifically, an aqueous solution of $HAuCl_4$ (1 mM, 20 mL) is stirred under reflux at 110° C. in an oil bath. An aqueous solution of trisodium citrate (38.8 mM, 2 mL) is added quickly into the aqueous solution of $HAuCl_4$, which results in a series of color changes before finally achieving a wine red solution. The wine red solution is stirred under reflux for about 10 minutes and is cooled to room temperature.

Figure 6:
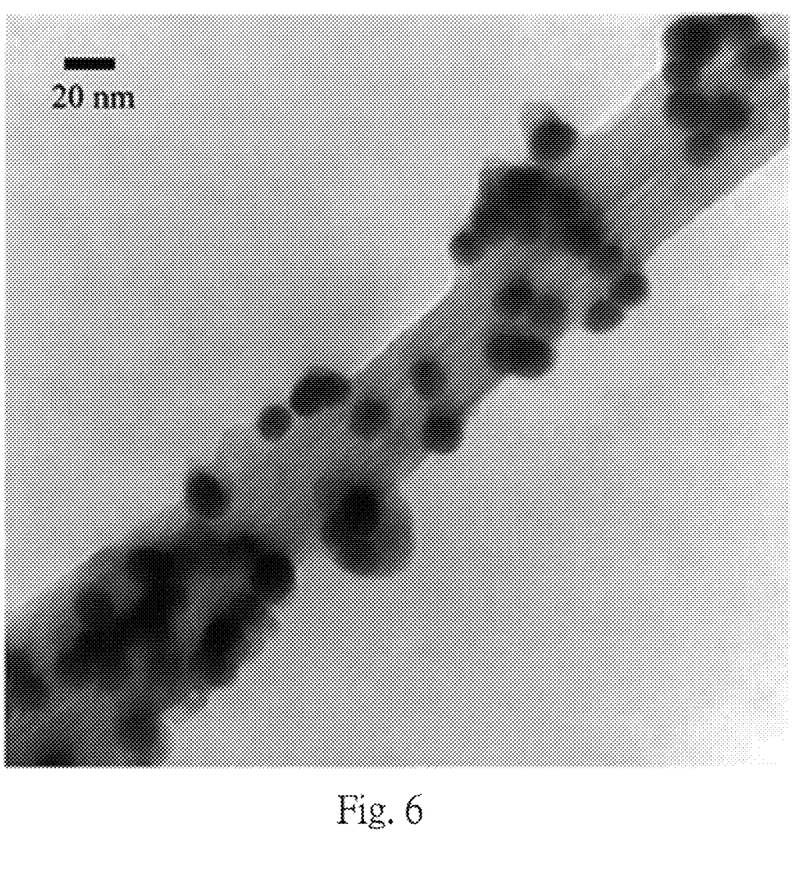
FIG. 6 is a high esolution transmission electron microscopy (HRTEM) image of a mixture of gold nanoparticles and thiolated carbon nanotubes according to another example of the present disclosure.

The gold nanoparticles are mixed with the thiolated carbon nanotubes so as to form a mixture. The mixture then is observed with a high-resolution transmission electron microscopy (JEOL JEM-2100F). FIG. 6 is a HRTEM image of the mixture of the gold nanoparticles and the thiolated carbon nanotubes. In FIG. 6, the thiolated carbon nanotubes are conjugated with the gold nanoparticles, which also proofs that the thiolation method for modifying the carbon nanotubes according to the present disclosure can successfully modify the surfaces of the carbon nanotubes with thiol groups, so that the thiolated carbon nanotubes can conjugate with the gold nanoparticles via thiol groups.

Sulfur Content of Thiolated Carbon Nanotubes

Figure 7A:
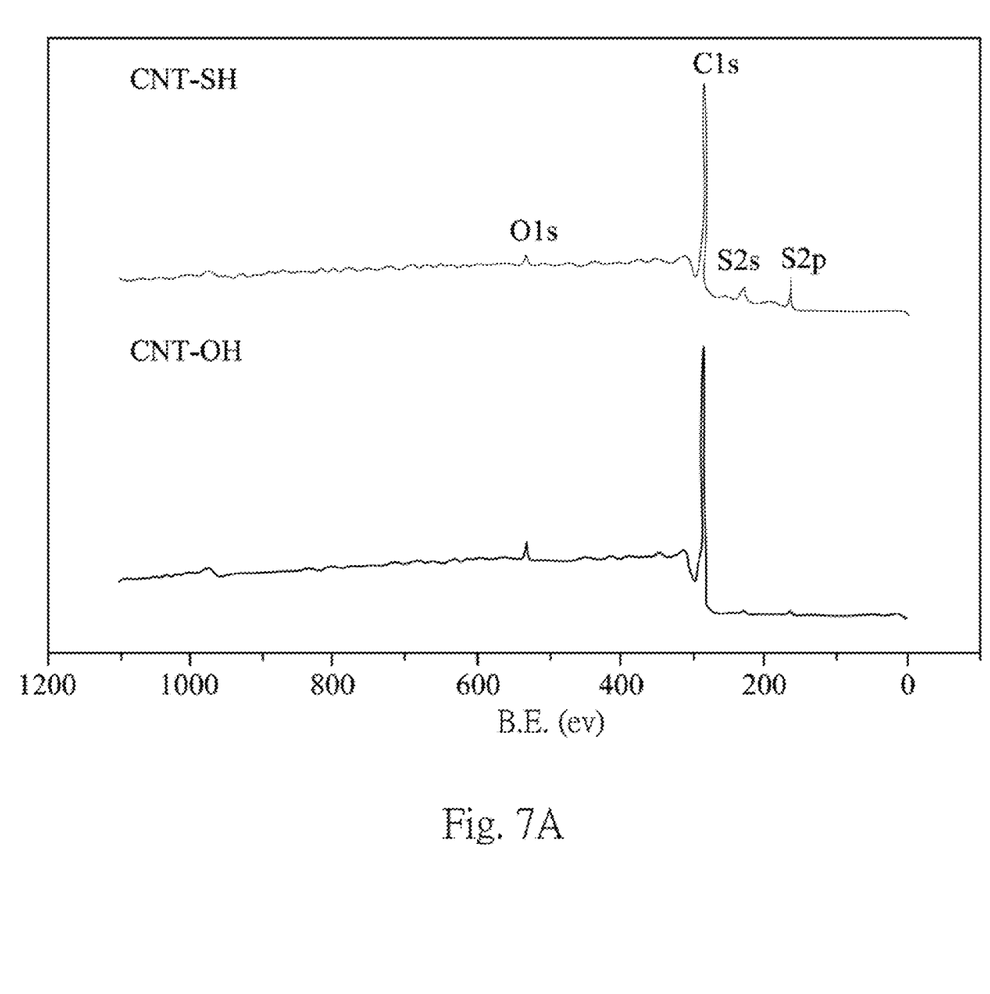
FIG. 7A shows X-ray photoelectron spectroscopy (XPS) spectra of hydroxylated carbon nanotubes and thiolated carbon nanotubes according to further another example of the present disclosure.
Figure 7B:
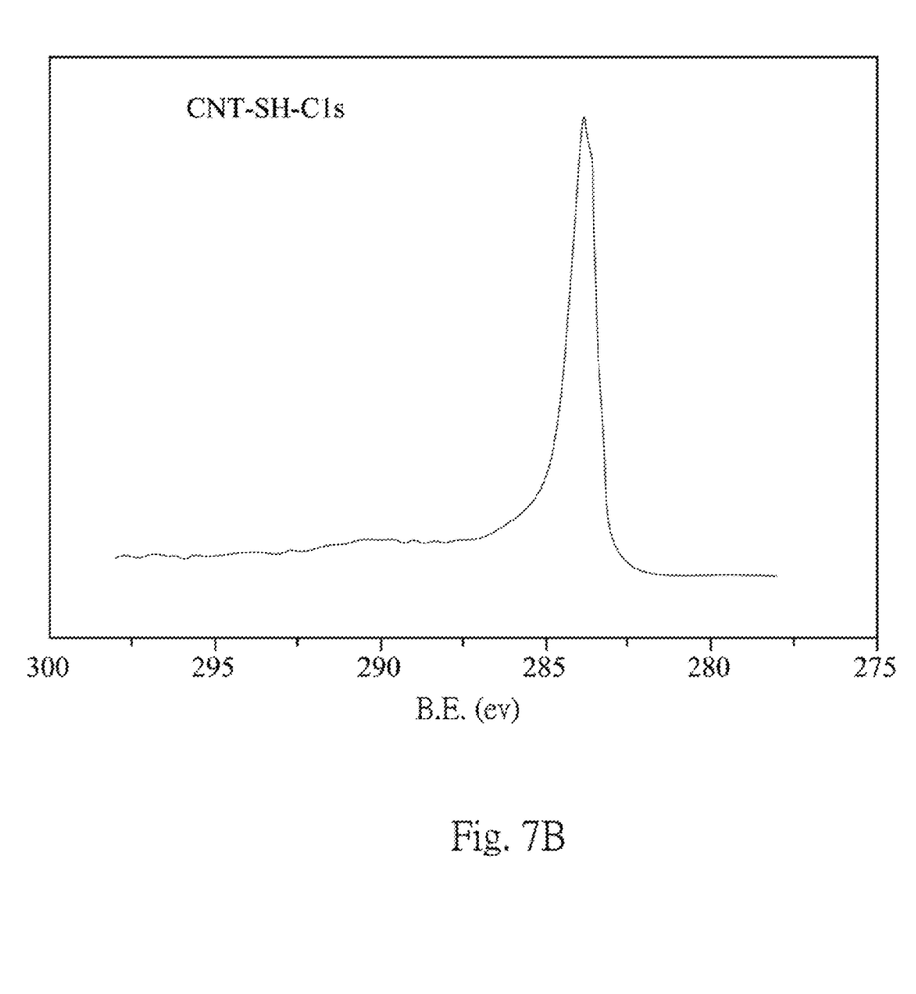
FIG. 7B is a partial enlarged view of the XPS spectrum of the thiolated carbon nanotubes in FIG. 7A.
Figure 7C:
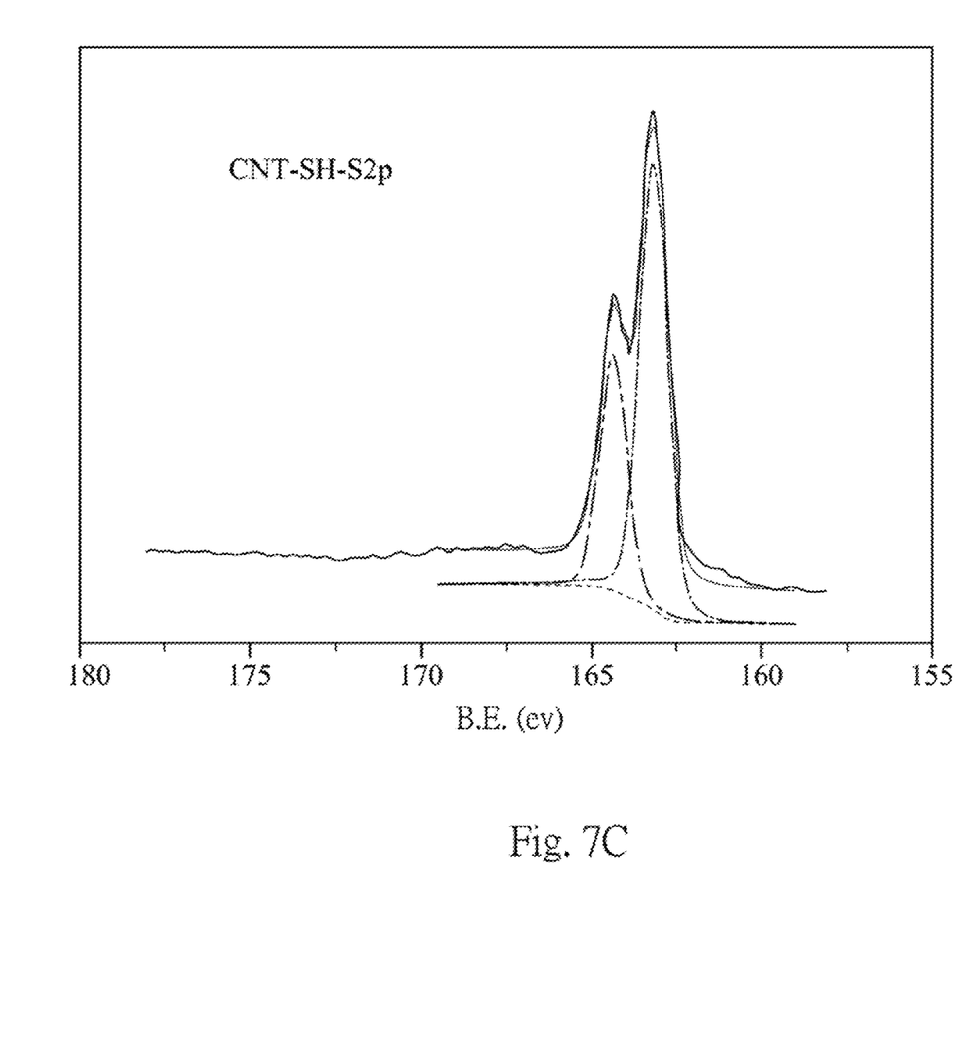
FIG. 7C is another partial enlarged view of the XPS spectrum of the thiolated carbon nanotubes in FIG. 7A.

FIG. 7A shows XPS spectra of hydroxylated carbon nanotubes (CNT-OH) and thiolated carbon nanotubes (CNT-SH) according to further another example of the present disclosure. FIG. 7B is a partial enlarged view of the XPS spectrum of the thiolated carbon nanotubes in FIG. 7A. FIG. 7C is another partial enlarged view of the XPS spectrum of the thiolated carbon nanotubes in FIG. 7A. In FIG. 7A, a $C_{1S}$ peak is observed at 283.85 eV, a $S_{2s}$ peak is observed at 228 eV, and a $S_{2p}$ peak is observed at 164 eV. In FIG. 7C, the peak fitting results reveals that the $S_{2p}$ peak is contributed by a $S_{2P}^{1/2}$— peak (164.35 eV) and a $S_{2P}^{3/2}$—H peak (163.2 eV). Furthermore, a sulfur content of the thiolated carbon nanotubes can be determined by the XPS spectrum of the thiolated carbon nanotubes. The sulfur content of the thiolated carbon nanotubes is about 6.55% (atomic percentage). It shows that a high content ratio of thiol groups can be conjugated on the surfaces of the carbon nanotubes. Accordingly, the application of the thiolated carbon nanotubes manufactured by the thiolation method according to the present is broader.

To sum up, the thiolation method for modifying the carbon nanotubes according to the present disclosure has advantages as follows. First, the thiol groups can be directly conjugated on the surfaces of the carbon nanotubes, and the physical properties of the carbon nanotubes can be maintained without the space linkers. Second, a specific and expensive equipment for plasma treatment is not required, thus the thiolation method has a low equipment cost and can be carried out in an ordinary laboratory. Third, the thiolated carbon nanotubes manufactured by the thiolation method according to the present disclosure has a high content ratio of the thiol groups, and the application thereof is broader.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:
1. A thiolation method for modifying carbon nanotubes, comprising:
providing a carboxylation step, wherein the carbon nanotubes are reacted with an oxidant for generating car- boxyl groups on surfaces of the carbon nanotubes so as to form carboxylated carbon nanotubes;

providing a hydroxylation step, wherein the carboxyl groups of the carboxylated carbon nanotubes are transformed into hydroxyl groups so as to transform the carboxylated carbon nanotubes into hydroxylated carbon nanotubes; and providing a thiolation step, comprising:
mixing the hydroxylated carbon nanotubes, a sulfur source and a first acidic substance and then stirring at a temperature ranging from 125° C. to 160° C. for 36 hours to 60 hours s a to form a first mixture, wherein the first acidic substance is hydrobromic acid, acetic acid, hydroiodic acid, chloric acid, perchloric acid, phosphoric acid or a mixture thereof;

adding the first mixture portion-wisely into an alkaline solution at a temperature ranging from 0° C. to 35° C. for 12 hours to 36 hours so as to form a second mixture, and acidifying the second mixture so as to form an acidified solution having a pH value ranging from 2 to 3, thus the hydroxylated carbon nanotubes are transformed into thiolated carbon nanotubes.

2. The thiolation method for modifying the carbon nanotubes of claim 1, further comprising:
providing a separation step, wherein the thiolated carbon nanotubes are separated from the acidified solution;
providing a washing step, wherein the thiolated carbon nanotubes are washed with a water; and
providing a drying step, wherein the thiolated carbon nanotubes washed with the water are heated to dryness.

3. The thiolation method for modifying the carbon nanotubes of claim 1, wherein the hydroxylation step comprises:
providing a reduction step, wherein the carboxylated carbon nanotubes, a reductant and a first solvent are mixed, and the carboxyl groups of the carboxylated carbon nanotubes are reduced so as to form a reaction solution; and
providing a hydrolysis step, wherein a second acidic substance is added into the reaction solution so as to obtain the hydroxylated carbon nanotubes.

4. The thiolation method for modifying the carbon nanotubes of claim 1, wherein an average outer diameter of the carbon nanotubes is greater than 0 μm and less than 8 μm, and an average length of the carbon nanotubes ranges from 10 μm to 30 μm.

5. The thiolation method for modifying the carbon nanotubes of claim 1, wherein the oxidant is an acid, ozone, potassium permanganate, potassium dichromate or a mixture of sulfuric acid and hydrogen peroxide.

6. The thiolation method for modifying the carbon nanotubes claim 5, wherein the acid is sulfuric acid, nitric acid, perchloric acid hydrochloric acid or a mixture thereof.

7. The thiolation method for modifying the carbon nanotubes of claim 1, wherein the carboxylation step is conducted at a temperature ranging from 15° C. to 120° C. for 3 hours to 84 hours.

8. The thiolation method for modifying the carbon nanotubes of claim 1, wherein a reductant is added in the hydroxylation step for transforming the carboxyl groups into the hydroxyl groups, and the reductant is lithium aluminium hydride ($LiAlH_4$), borane ($BH_3$), sodium tetrahydridoborate ($NaSH_4$) or a Fenton reagent.

9. The thiolation method for modifying the carbon nanotubes of claim 3, wherein the first solvent is anhydrous ether or anhydrous tetrahydrofuran.

10. The thiolation method for modifying the carbon nanotubes of claim wherein the reduction step is conducted at a temperature ranging from 40° C. to 80° C. for 20 hours to 30 hours.

11. The thiolation method for modifying the carbon nanotubes of claim 3, wherein the second acidic substance is hydrochloric acid, sulfuric acid, hydrobromic acid, hydroiodic acid or acetic acid.

12. The thiolation method for modifying the carbon nanotubes of claim 1, wherein the sulfur source in the thiolation step is thiourea or thioaceti acid.

13. The thiolation method for modifying the carbon nanotubes of claim 1, wherein a pH value of the first acidic substance in the thiolation step ranges from 0 to 2.

14. The thiolation method for modifying the carbon nanotubes of claim 1, wherein a pH value of the alkaline solution in the thiolation step ranges from 10 to 14.

15. The thiolation method for modifying the carbon nanotubes of claim 1, wherein the alkaline solution in the thiolation step is a sodium hydroxide solution or a potassium hydroxide solution.

16. The thiolation method for modifying the carbon nanotubes of claim 1, wherein a temperature of the alkaline solution in the thiolation step ranges from 0° C. to 30° C.

17. The thiolation method for modifying the carbon nanotubes of claim 1, wherein a concentration of the alkaline solution in the thiolation step ranges from 5 weight percentage to 30 weight percentage.

18. The thiolation method for modifying the carbon nanotubes of claim 1, wherein the second mixture is acidified by adding sulfuric acid, hydrochloric acid, hydrobromic acid, hydroiodic acid or acetic acid into the second mixture.

19. The thiolation method for modifying the carbon nanotubes of claim 18, wherein a concentration of the sulfuric acid, the hydrochloric acid, the hydrobromic acid, the hydroiodic acid or the acetic acid ranges from 35weight percentage to 75 weight percentage.

20. The thiolation method for modifying the carbon nanotubes of claim 1, wherein the second mixture is acidified at a temperature ranging from 0° C. to 15° C.

21. The thiolation method for modifying the carbon nanotubes of claim 2 wherein the drying step is conducted at temperature ranging from 40° C. to 80° C. for 16 hours to 32 hours.

* * * * *